United States Patent [19]
Leveen et al.

[11] Patent Number: 5,520,632
[45] Date of Patent: May 28, 1996

[54] ASCITES VALVE

[75] Inventors: Robert F. Leveen, Philadelphia, Pa.;
Eric G. Leveen, Charleston, S.C.

[73] Assignee: Robert Leveen, Omaha, Nebr.

[21] Appl. No.: 683,821

[22] Filed: Apr. 11, 1991

[51] Int. Cl.⁶ ................................................. A61M 27/00
[52] U.S. Cl. ....................................................... 604/9; 604/8
[58] Field of Search ............................ 604/8, 9, 10, 93, 604/128, 149; 138/120

[56] References Cited

U.S. PATENT DOCUMENTS

| | | | |
|---|---|---|---|
| 3,810,283 | 10/1975 | Leveen | 604/9 |
| 4,261,341 | 4/1981 | Hakim et al. | 604/9 |
| 4,464,168 | 8/1984 | Redmond et al. | 604/9 |
| 4,553,956 | 11/1985 | Muller | 604/9 |
| 4,650,463 | 3/1987 | Leveen et al. | 604/128 X |
| 4,662,404 | 5/1987 | Leveen et al. | 138/120 |
| 4,795,437 | 1/1989 | Schulte et al. | 604/10 |
| 4,904,236 | 2/1990 | Redmond et al. | 604/9 |
| 4,904,241 | 2/1990 | Bark | 604/93 |
| 5,026,344 | 6/1991 | Dijkstra et al. | 604/93 |

FOREIGN PATENT DOCUMENTS 8301387 4/1983 WIPO ........................................ 604/9

OTHER PUBLICATIONS

Harry H. LeVeen, M.D. and Ruth B. Hutto, RN, MA; "Complications of the Peritoneovenous Shunt"; *Problems in General Surgery*, vol. 2, No. 1; pp. 82–92; Jan. 1985.
Harry H. LeVeen, M.D., Thomas Brown, M.D., and Nicola G. d'Ovidio, M.D.; "Surgical Treatment of Ascites"; *Advances in Surgery*, vol. 14; pp. 107–150; 1980.

Harry H. LeVeen; "The Peritoneovenous Shunt: Inception to Maturity"; *ASAIO*; vol. 36, No. 2; pp. 50–55; Apr.–Jun., 1990.
Harry H. LeVeen, M.D., George Christoudias, M.D., Moon Ip, M.D., Richard Luft, M.D., Gerald Falk, M.S., and Saul Grosberg, M.D.; "Peritoneo–Venous Shunting for Ascites"; *Annals of Surgery;* vol. 180, No. 4; pp. 580–591; Oct., 1974.
Harry H. LeVeen, M.D., Simon Wapnick, M.D., Carlos Diaz, M.D., Saul Grosberg, M.D., and Michael Kinney, M.D.; "Ascites: Its Correction by Peritoneovenous Shunting"; *Current Problems In Surgery;* pp. 1–61; 1979.

*Primary Examiner*—Sam Rimell
*Attorney, Agent, or Firm*—Gipple & Hale; John S. Hale

[57] ABSTRACT

A device for the transfer of body fluids which accumulate in the peritoneum cavity into the vascular system comprising a peritoneal tube connected to the inlet chamber of a hollow plastic implanted valve assembly, causing a valve to open and passing the fluid under pressure into a second reservoir from where the fluid is conducted through a venous tubing which is connected to the jugular vein of the patient. The valve assembly comprises a plastic housing with an inlet and outlet, the peritoneal tube being secured to the inlet leading to an inlet reservoir located within the valve housing and the venous tube being secured to the outlet leading from the outlet reservoir located within the valve housing. The valve housing defining a valve seat and having a flexible diaphragm valve which rests against the valve seat and moves away from said valve seat in response to pressure exerted thereon to permit flow of the body fluid from the peritoneum through the valve housing and into the venous tubing which is threaded into a major intrathoracic vein via the internal jugular vein or other alternate access veins.

10 Claims, 13 Drawing Sheets

ASCITES VALVE

BACKGROUND OF THE INVENTION

Ascites is a common complication of cirrhosis and carcinoma. Its presence significantly worsens the prognosis. A high percentage of patients having cirrhosis who do not respond to a salt restricted diet are dead within a year. Mortality in such patients is due to renal failure brought about by diminished renal perfusion secondary to a diminished blood volume (Clairmont, R. J., Gastroenterol., 1967, 53:220–228). The peritoneovenous shunt has been a significant advance in the therapy of this condition. Ascitic fluid has its ultimate origin from blood and should be returned to the circulating blood from where it arose. The shunt drains ascitic fluid from the peritoneal cavity via flexible tubing through a sensitive, one-way, pressure activated valve into a tube whose tip is located in a major thoracic vein. The shunt system thus continuously infuses ascitic fluid into the blood. The descent of the diaphragm during respiration lowers the pressure in the thorax to below atmospheric pressure enabling air to enter the lungs. The force required to pump the fluid is supplied by a differential pressure between the peritoneal fluid and a large intrathoracic vein. This differential pressure is brought about by a negative intrathoracic pressure which occurs during respiration with descent of the diaphragm and a simultaneous increase in intraperitoneal pressure as the descent of the diaphragm decreases the volume of the peritoneal cavity. Once the fluid gains access to the circulating blood, the body excretes any excess fluid as urine. Although excessive amounts of water and salt are excreted by the kidney, the plasma proteins present in the ascitic fluid are retained.

Flow sensitive valves require a small amount of backflow to close the valve orifice. A small amount of backflow into the venous tubing will obstruct it with clots. A normally closed sensitive pressure activated valve is mandatory to prevent regurgitation of blood into the tubing (LeVeen, H. H., Ann. Surg., 1974, 180:580). A normally closed pressure sensitive valve prevents backflow of blood into the venous tubing which would obstruct the lumen with clots. An obstruction to the free flow of ascitic fluid into the venous system results in failure of the shunt. Although the valve must be normally closed, the valve must open at very low pressures (1 to 4 cm of water) since the differential pressures which supply the necessary pumping force are extremely low. The diaphragm of the valve is manufactured of a low durometer biocompatible elastomer such as silicone rubber together with the struts which suspend the diaphragm over the valve's seat. The struts being elastomeric elongate with pressure and allow the diaphragm to rise and open the valve at low pressures.

DESCRIPTION OF THE PRIOR ART

In U.S. Pat. No. 3,910,283, the flexible diaphragm valve of the valve is shown occupying the transverse diameter of a cylindrical rigid opaque plastic housing.

A diaphragm valve offers the lowest resistance to flow as compared to other configurations, e.g., a spring loaded ball valve or a duck bill valve. When open, a diaphragm valve offers little resistance to flow because the diaphragm can cover an opening of large cross sectional area thus amplifying the opening force and reducing resistance to flow.

The resistance (R) to flow of Newtonian fluids through a tubular structure depends on the length (L) and radius (r) of the tube and the viscosity of the fluid (z) according to the equation of Poiseuille:

$$R = \frac{8Lz}{\pi r^4} \quad \text{(Poiseuille's Law)}$$

In the '283 Patent, the inflow and outflow ports of the valve were at the opposite ends of a circular housing. Regurgitation of blood was prevented since the valve was normally closed with sufficient sensitivity to open at differential pressures of 1 to 4 centimeters of water.

The physical configuration of this valve is unsatisfactory since the housing is large in its transverse diameter because the transverse diameter of the elastomeric diaphragm is very large. Since the valve body or housing was fabricated of relatively opaque rigid plastic (polypropylene), the opening and closing of the valve during respiration could not be detected at surgery. However, it is necessary that the surgeon confirm that the valve is functioning before closing the incisions. The cylindrical housing of the valve of the '283 Patent is cumbersome since the valve must occupy a considerable depth in the subcutaneous tissue. Ideally, the largest dimension of the housing enclosing the diaphragm should lie in the same plane as the subcutaneous fatty tissue which is parallel to the skin.

Furthermore, the valve and body of the shunt system as described in the '283 Patent made no provision for entering the shunt system using a syringe and needle. The venous side of the shunt system should incorporate an injection port which can be accessed easily with a syringe and needle. Alternatively, the soft silicone self sealing injection portal could be placed close to the outlet port of the valve and could be configured as a bubblelike expansion of the venous tubing. This is easily felt and can be identified by palpation and entered with a fine needle.

Also, the '283 Patent described only the valve portion of the shunt and ignored the venous and peritoneal tubes which are equally important and must be considered in the logistics of design. The peritoneal drainage tubing of the present invention was designed for simple and rapid insertion and removal and prevention of problems. Previously, the peritoneal drainage tube was merely a flexible tube with perforated side holes. This has proved to be unsatisfactory because fat lobules from the omentum frequently enter the small holes of the tubing and become incarcerated. Incarcerated lobules are avulsed if removal of the peritoneal tubing becomes necessary. This trauma to the omentum frequently causes serious intraperitoneal bleeding since most of these patients have high intravascular pressures secondary to portal hypertension. At other times, these fat lobules have broken off and embolized to the valve thus blocking the flow of ascitic fluid or rendering the valve incompetent causing obstructive clots in the venous tubing.

SUMMARY OF THE INVENTION

In the present invention, the configuration of the valve housing is that of a thin disc with the largest dimension of the housing lying parallel to the skin and subcutaneous fatty tissue. This avoids the lump previously caused by the large mound of tissue necessary to cover the valve. A valve housing made of a biocompatible transparent plastic was configured so that the inflow and outflow orifices could be at the edges of the thin disc shaped housing. Transparency not only allows the surgeon to observe valve function but permits the detection of fibrin deposits, blood or debris in the ascitic fluid. The large transverse diameter of the housing can now lie in the plane of the skin and subcutaneous tissue without causing a protusion. An arrow on the upper surface of the valve shows the direction of flow. This warns against inadvertently connecting the valve in the reverse direction of flow. The elastomeric diaphragm of the valve is held in place by a circular ridge around the valve seat and is held firmly against the circular ridge by small projections extending downward from the disc cover to compress the elastomeric ring. The cover on the outlet side contains a soft biocompatible elastomeric injection port such as a low durometer silicone rubber. An alternate place for the injection port is in the form of a bubblelike expansion of the venous tubing close to the outlet port of the valve.

The present invention contains such a portal permitting injections or aspirations for diagnostic and therapeutic purposes. A small circular opening in the cover on the outlet side of the valve contains a soft silicone rubber plug which is self sealing after a needle puncture. Shunt failure is not uncommon and requires an exact diagnosis of the cause (LeVeen, H. H., Ann. Surg. 1984, 200:212). An injection of a radio opaque solution into the venous side of the valve often makes it possible to differentiate obstruction of the peritoneal portion of the shunt from that of obstruction to the venous portion of the shunt. Alternatively, the soft silicone self sealing injection portal could be placed close to the outlet port of the valve and could be configured as a bubblelike expansion of the venous tubing. This is easily felt and can be identified by palpation and entered with a fine needle.

The modular design of the present invention permits an easy replacement of any failed part. The individual replacement of the failed part of the shunt is therefore possible without removal of the entire shunt system. Fresh clots in the venous tubing or vena cava can be dissolved by injecting fibrinolysins. Reopening of a clotted venous tubing often prevents a second neck incision which is painful to the patient and distressing to the surgeon.

In the accompanying drawings, there is shown an illustrative embodiment of the invention from which these and other of objective, novel features and advantages will be readily apparent.

DETAILED DESCRIPTION OF THE DRAWINGS

The peritoneal tubing, valve and valve housing of the present invention has been designed to prevent the aforementioned complications which are noted as occurring in U.S. Pat. No. 4,650,463. The preferred embodiment and best mode of the invention is shown in FIGS. 1–6.

Figures 1, 2, 3:
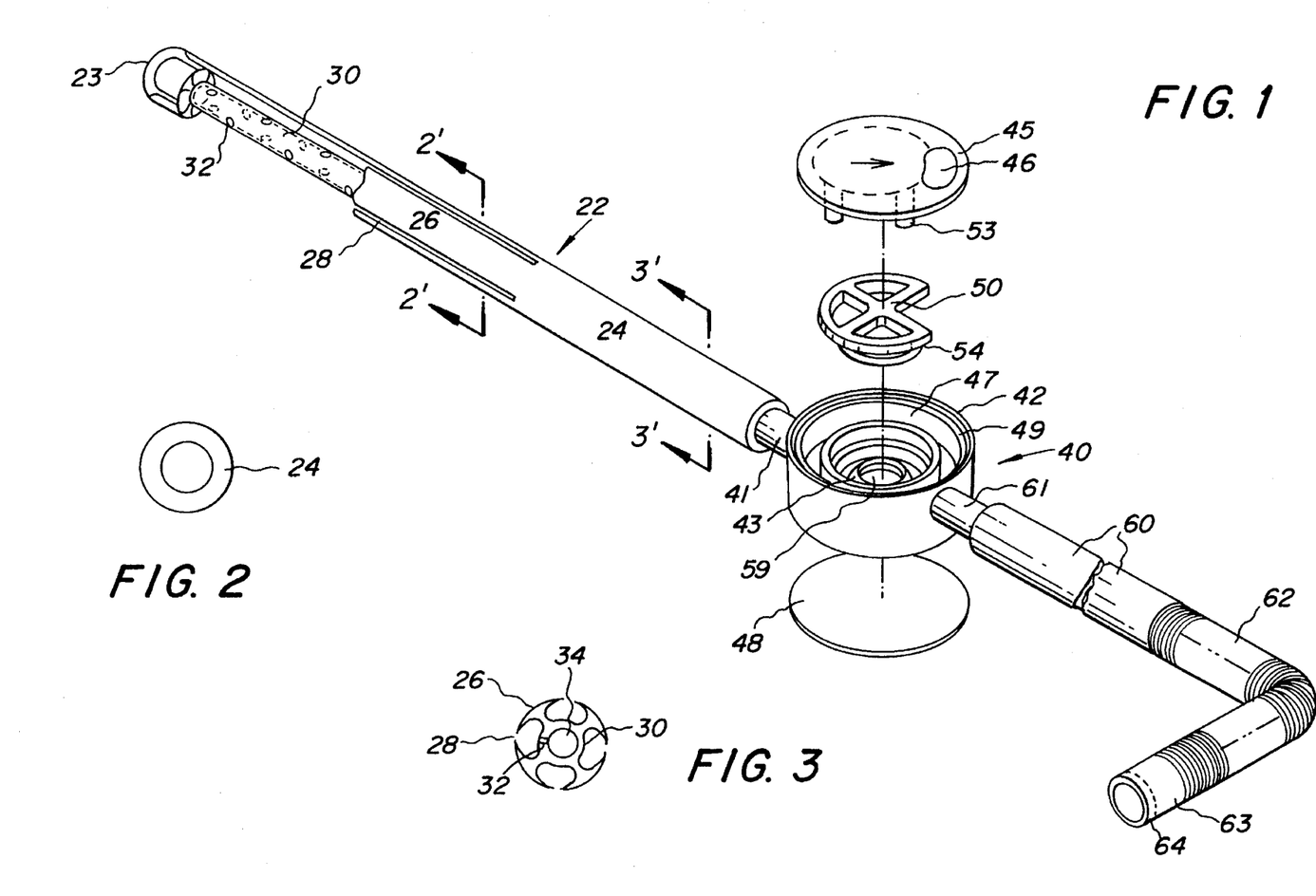
FIG. 1 is an exploded view of the inventive shunt assembly.
FIG. 2 is a cross section view of the peritoneal tubing of the inventive shunt assembly taken along lines 2'—2' of FIG. 1.
FIG. 3 is a cross section view of the peritoneal tubing of the inventive shunt assembly taken along lines 3'—3' of FIG. 1.

FIG. 1 shows an exploded view of the ascites shunt assembly 20. The various component parts are welded together by heat sealing or adhesives rather than by threaded members which are prone to leak. The flexible peritoneal tubing 22 is shown in its entirety while the venous tubing 60 is shown broken away. That portion of the peritoneal tubing which perforates the abdominal wall is designated by the number 24 and has a circular cross section as shown in FIG. 2. The peritoneal portion 26 of the tubing 22 is provided with throughgoing longitudinal slits 28. These slits 28 allow communication with a small circular tube 30 which is concentrically positioned from the axis of the center of the tubing and contains throughgoing perforations 32 into its center lumen 34. A cross section view of this construction is shown in FIG. 3. The longitudinal slits 28 hold out the omentum and any omentum gaining access to the small segmental compartment formed by the inner wall of the outer tube portion 26 and the outer wall of tube 30 and thus would be unable to reach the perforations in that segment. Removal of the tubing does not traumatize the omentum and cause bleeding. It will be noted that the end portion 23 of the peritoneal tubing 22 which perforates the abdominal wall has an outside shape which is rounded and without protuberances or slits. That portion of the tubing which is inside the peritoneal cavity has long longitudinal slits 28 on the outer circumference of the tube. These slits open into an inner lumen 34 via perforations 32. These long longitudinal slits allow any incarcerated omental lobules to slide along the slit during removal of the tube, thus preventing their avulsion. That part of the collecting tube 24 which exits the abdominal wall is circular and contains no slits to ensure a leak free seal between the tube and the abdominal wall. The tubing permits easy insertion and removal since it has a smooth outer circular configuration. The peritoneal tubing is easily inserted into the peritoneal cavity by means of an introducer utilizing the Seldinger technique.

Figure 4:
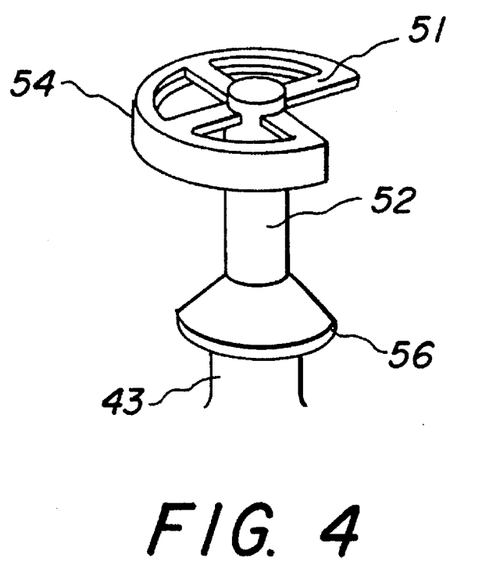
FIG. 4 shows an isolated perspective view of the valve seat, valve and elastomeric struts in a normally shut position.
Figure 5:
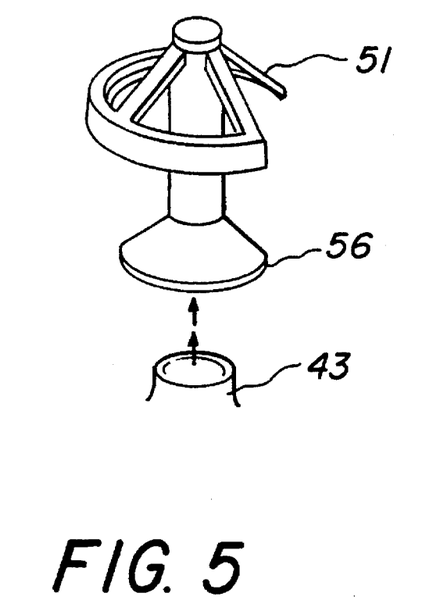
FIG. 5 shows an isolated perspective view of the valve seat, valve and elastomeric struts in an open position.

The peritoneal collection tubing 22 is attached to a nipple shaped connector 41 which is the inlet port of valve 40. The rigid cylindrical body 42 of the valve 40 is formed with two separated compartment reservoirs and is fabricated of transparent plastic so that the surgeon may see the valve open and shut during respiration as illustrated in FIGS. 4 and 5. The body of the cylindrical valve is made of a transparent biocompatible plastic such as polysulphone which has good optical clarity and engineering plastic properties and is integrally molded with an intermediate inwardly projecting support wall supporting conical valve seat 43 and a valve retaining wall 47 upon which valve diaphragm 56 rests. The support wall and valve seat divide the valve housing into an inlet chamber or reservoir and an outlet chamber or reservoir. The cover 44 on the outlet side, which is the upper surface of the valve, is provided with a small circular opening 45 which contains a soft silicone injection plug 46. The plug 46 is bonded to the plastic of lid 45 and not held in place by mechanical forces. The plug 46 is self sealing after a needle puncture. The cover 44 rests on cover seat 49 formed on the inner wall of cylindrical body 42 with the circumference of the cover abutting the inner wall of valve body 42. A bottom cover 48 is secured to the bottom of the cylindrical valve body 42 in the same manner as previously described for cover 44. If desired, the covers could be snap fit into grooves cut in the inner surface of body 42. The valve member 50 has elastomeric struts 51 extending from the proximal end of stem 52 connected to and reinforced by rim member 54. The distal end of stem 52 is provided with a conical diaphragm member 56 which sits on seat 43 which defines port 59. As previously noted, the diaphragm 56 sits on seat 43 and is held in place by projection members 53 which downwardly project from cover 44 and engage the rim member 54 while the diaphragm 56 is held in place by retaining wall 47. Thus the valve is kept in the normally shut position as shown in FIG. 4. The differential pressure of 1–4 cm of water stretches the elastomeric struts and lifts the valve diaphragm 56 above the valve seat orifice 59 as is clearly shown in FIG. 5. The diaphragm of the valve is manufactured of a low durometer silicone rubber together with the struts which suspend the diaphragm over the valves inlet orifice. The struts being elastomeric elongate with pressure and allow the diaphragm to raise and open the valve at low pressures.

It will be apparent to anyone skilled in the art that the thickness of the elastomeric struts 51 are important in determining the opening pressure of the valve and the resistance to flow through the valve at low differential pressures. Also important in the opening pressure is the degree of tensile strain on the struts in the closed position. If there is practically no tension on the struts as in FIG. 4, the opening pressure will be low. While a low opening pressure is important in ascites as previously described, in the ventriculoperitoneal shunt for hydrocephalus, the opening pressure must be higher to avoid sagging of brain tissue. In hydrocephalus the sensitivity must not be as low as required for ascites since the volume of the fluid to be cleared is far less than in ascites and large fluctuations in pressure and volume must be avoided. Thicker struts dampen fluctuations and tend to maintain a mean pressure which is very desirable in the therapy of hydrocephalus. The design of the valve itself therefore lends itself to usage for conditions other than ascites such as hydrothorax and hydrocephalus.

The venous tubing 60 is circular and thin walled. The venous tubing 60 is attached to a nipple shaped connector 61 which is the outlet port of valve 40. The tubing is reinforced with circular radio opaque bands 62 which are rigid and placed more frequently than two times the diameter of the tubing, thus rendering the venous tubing kink proof in those areas where bending is required.

Figure 6:
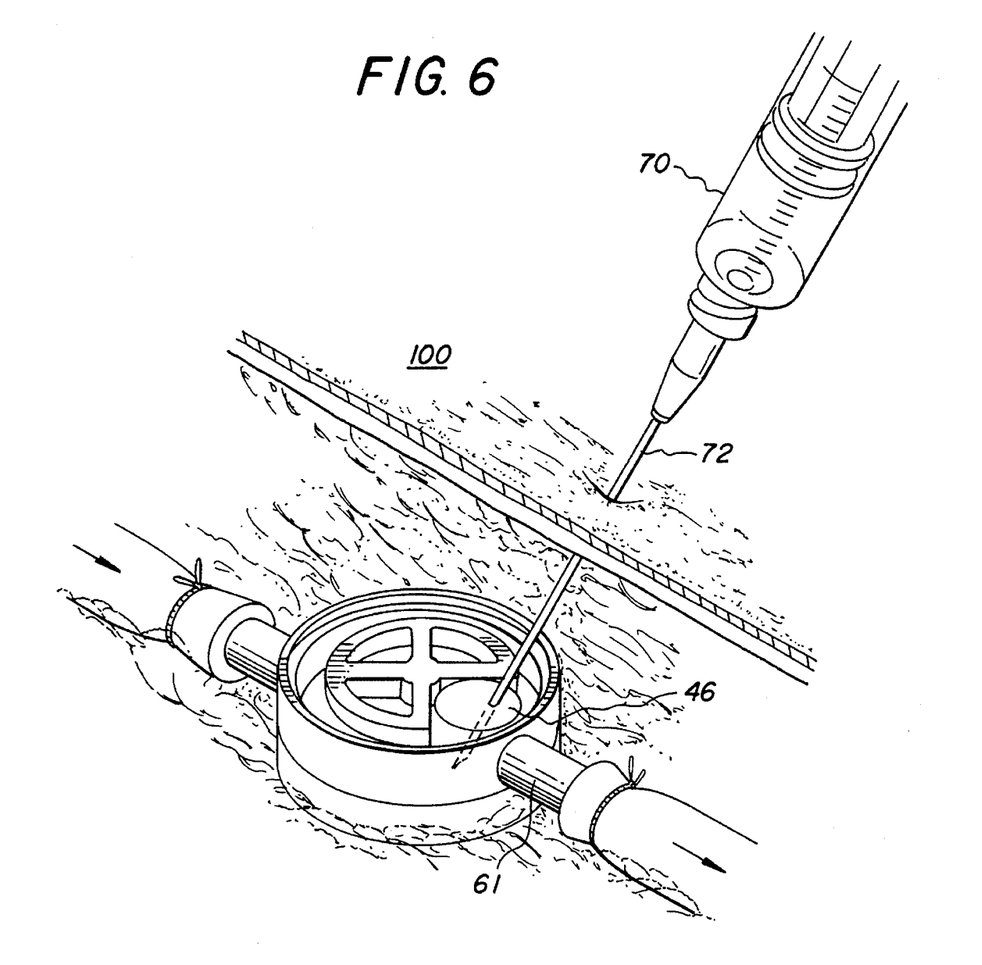
FIG. 6 is an enlarged perspective view of the disc shaped valve housing implanted in the patient with body portions cut away with peritoneal and venous tubing tied to the inlet and outlet ports and a syringe inserting fluid into the valve outlet chamber.

FIG. 6 shows a syringe 70 and needle 72 inserted through the skin 100, subcutaneous fatty layer 102 and the soft injection pad 46 into the outlet valve housing chamber. The injection pad 46 can be easily located with needle 72 since it is at the base of the outlet portal of the valve body. A syringe attached to the needle makes it possible to inject medicaments or radio opaque compounds into the outlet side of the valve and the venous tubing.

Figure 6A:
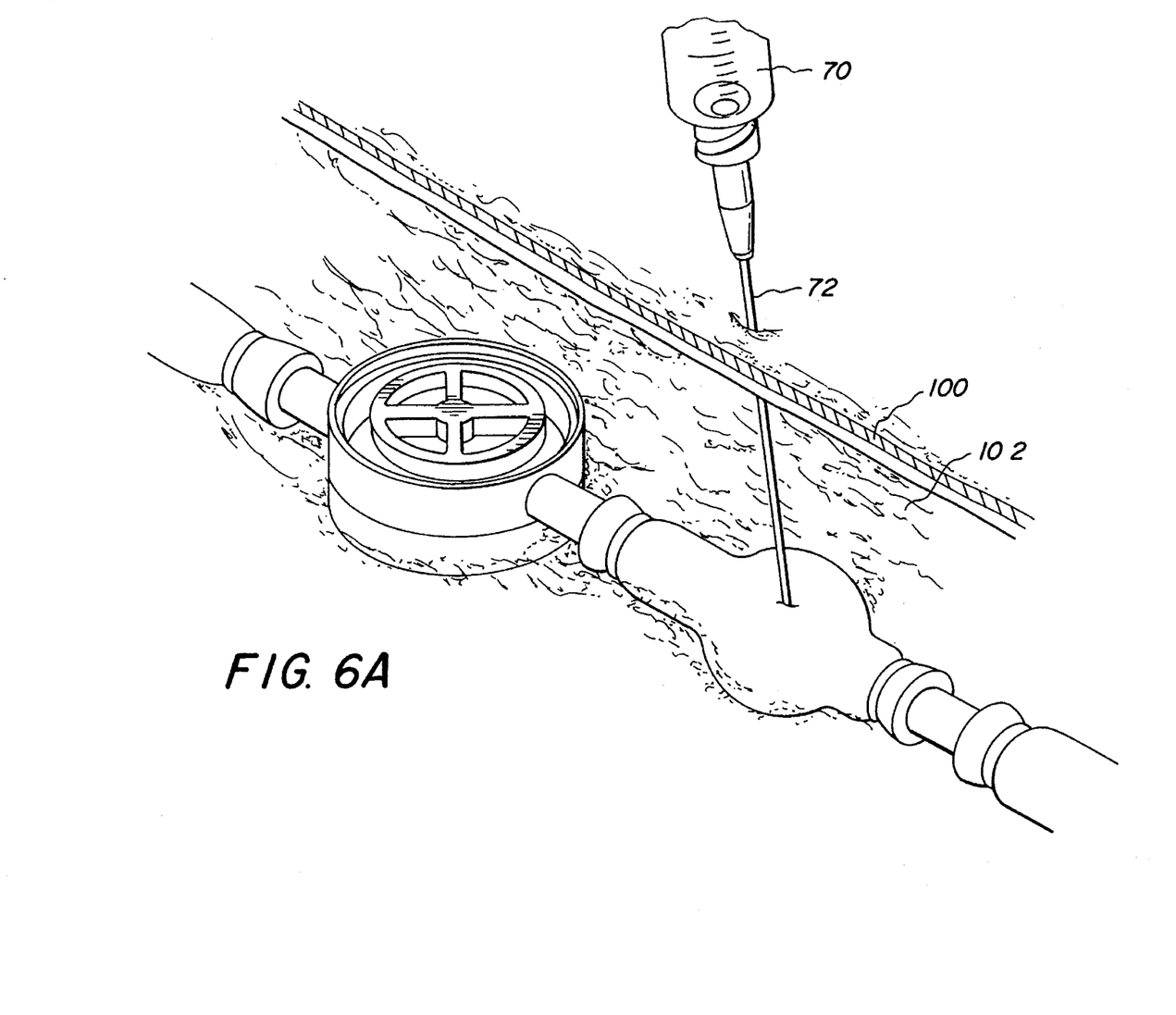
FIG. 6A shows the alternate location of an access portal with a needle entering a sealable injection port as in FIG. 6. In this situation, the cover of the valve is solid and contains no portal for needle puncture into the outlet chamber of the valve. Since the dilated injection portal is easily located by palpation, its injection is simple.

FIG. 6A which is the alternate location for an access portal shows a syringe 70 with an attached needle 72 inserted through the skin 100 and subcutaneous fatty tissue 102 as in FIG. 6 but instead entering a soft silicone bubble attached to the venous tubing near the outlet port. The syringe attached to the needle makes it possible to inject radiopaque compounds into the venous tubing at the outlet side of the valve. Also, pharmaceuticals such as those which produce clot lysis can be injected to dissolve any clots which may form in the vena cava or other veins.

The insertion of the peritoneal and venous tubing into the patient 200 is shown in FIGS. 7–18.

Figure 7:
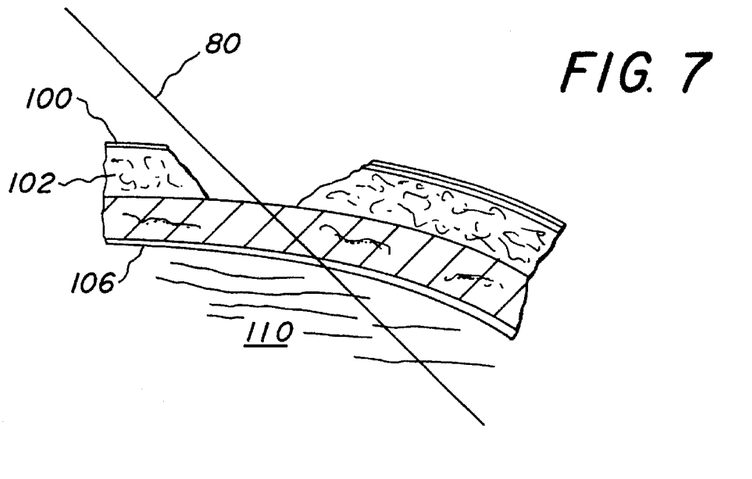
FIG. 7 shows a schematic insertion of a guide wire into the peritoneal cavity.

FIG. 7 shows a guide wire 80 inserted through the abdominal wall 106 into the peritoneal cavity 110.

Figures 8, 9:
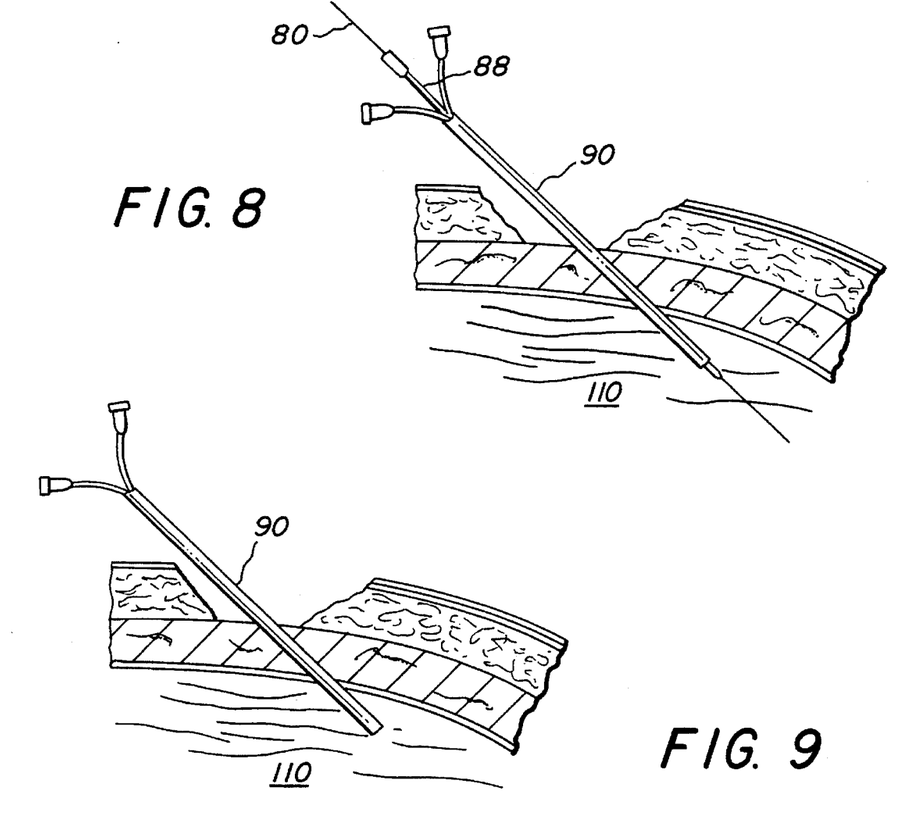
FIG. 8 shows a schematic sequential insertion of the dilator and strip tube over the guide wire into the peritoneal cavity.
FIG. 9 shows a schematic sequential removal of the guide wire and dilator from the strip tube.

FIG. 8 shows a dilator 88 and an introducer 90. The dilator 88 is inserted over the guide wire 80 to a diameter which will allow the passage of the peritoneal tubing 22.

In FIG. 9 the introducer 90 is shown after removal of the dilator and guide wire.

Figure 10:
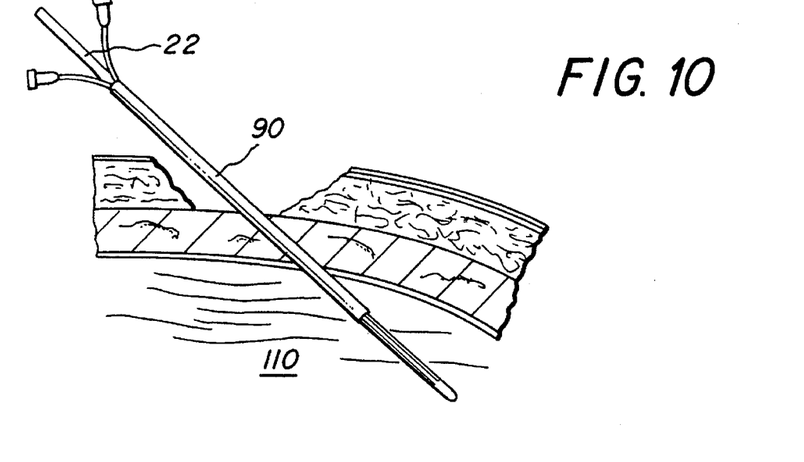
FIG. 10 shows a schematic sequential insertion of the peritoneal tubing through the strip tube into the peritoneal cavity.

In FIG. 10 the peritoneal tubing 22 has been inserted through the introducer 90.

Figures 11, 12:
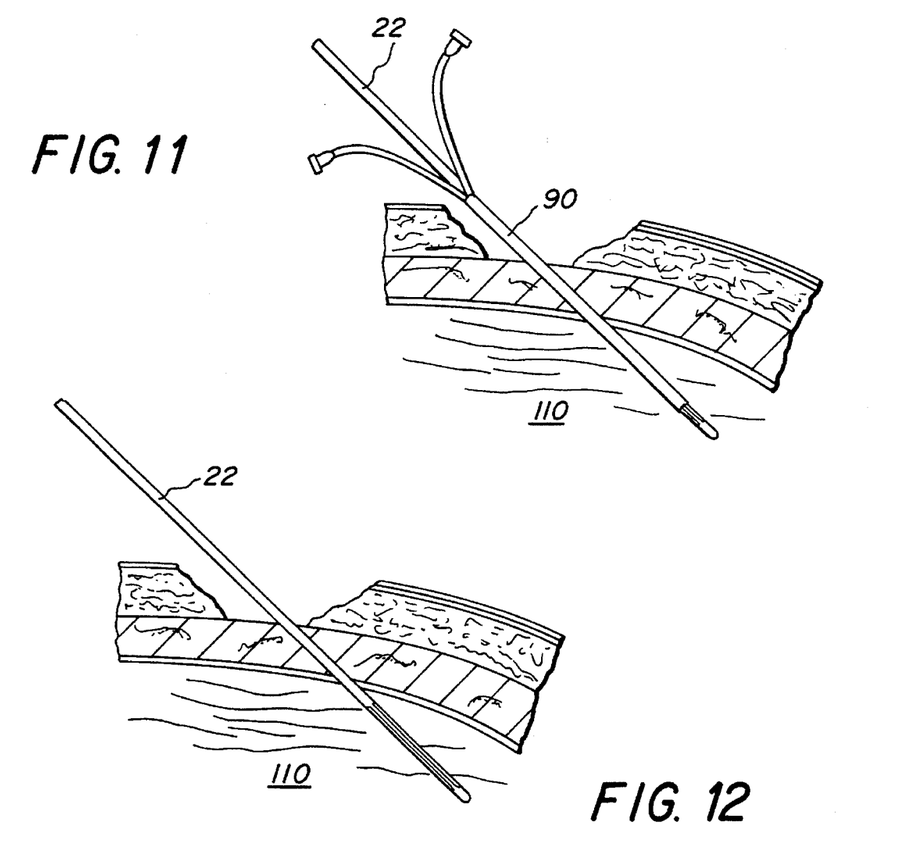
FIG. 11 shows a schematic sequential of how the introducer is peeled away from the peritoneal collecting tube.
FIG. 12 shows a schematic sequential after removal of the introducer leaving the peritoneal tubing in the peritoneal cavity.

In FIG. 11 the introducer 90 is split by pulling it apart and removing it.

In FIG. 12 the peritoneal tube 22 is seen in the peritoneal cavity 110.

In FIGS. 7–12 a subcutaneous incision is made at a suitable site on the upper abdomen to expose the abdominal musculature. A needle is diagonally inserted into the peritoneal cavity 110 through the abdominal musculature 106. A flexible guide wire 80 is introduced through the bore of the needle which is then removed leaving the guide wire in place. In FIG. 7 a dilator 88 and introducer sheath 90 are placed over the guide wire 80 and the small needle hole is dilated to the size which will accommodate the splitable introducer 90 shown in FIG. 8. The rigid dilator 88 is then removed leaving the circular introducer 90. Before removing the introducer, some surgeons prefer to aspirate some peritoneal fluid. After an appropriate quantity has been removed, the peritoneal collection tube 22 is inserted as shown in FIG. 10 and the introducer is removed by splitting the two sides (FIG. 11).

The lower section 26 of the peritoneal collecting tube 22 is positioned in the peritoneal cavity 110. The upper part 24 of the tube 22 contains no slits and fits so tightly in the tissues 100–108 that there is little or no leakage of ascitic fluid around its circumference. Further aspiration of fluid can also be done at this time before connecting the peritoneal tubing to the valve. Leakage of ascitic fluid constituted a problem when the shunt in U.S. Pat. No. 3,910,283 was inserted, because it required incision to be made into the peritoneal cavity 110. A subsequent difficulty occurred in completing a water tight closure of the peritoneum 108 around the valve which is predisposed to leakage.

The present invention utilizes an introducer which requires only a needle puncture that is dilated to accept the tubing and leakage is almost never a problem. After cutting off excess tubing, the peritoneal collection tubing is then attached to the inlet port of the valve which has a nipple shaped connector 41 to accept an elastomeric tubing. The valve lies in an incision made through the subcutaneous fat 102. Some of the fat and deep fascia are dissected so that the valve 40 lies quite flat against the abdominal wall. This allows the skin 100 and subcutaneous tissue 102 to be easily closed over it without tension.

Figure 13A:
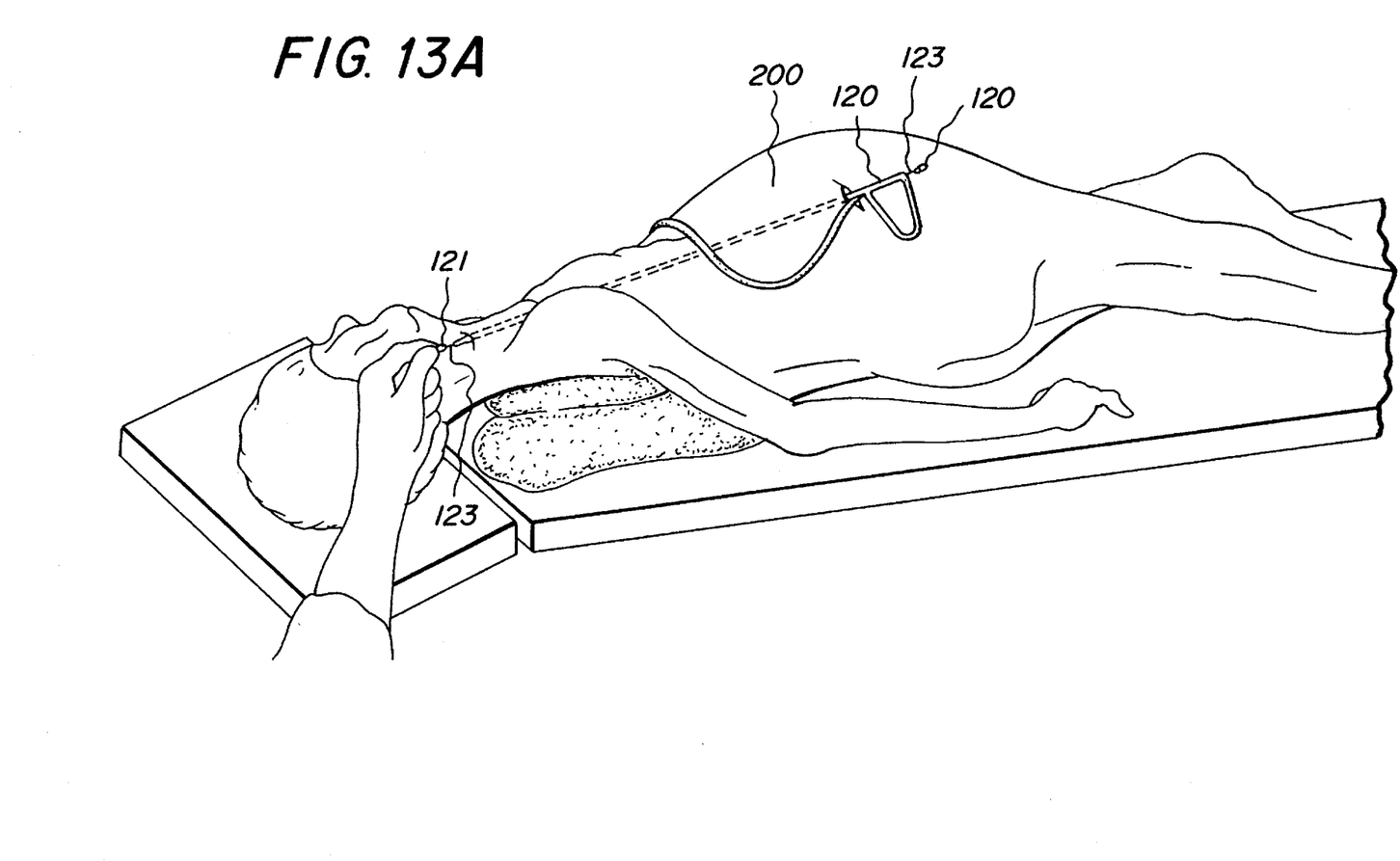
FIG. 13A shows the schematic representation of a sequential step required to bring the venous tubing from an abdominal incision into a neck incision using the vein and tubing passer of U.S. Pat. No. 4,418,693, in which a rigid metal tube is thrust through the subcutaneous tissue from an abdominal wound in to a neck wound wherein the surgeon grasps the bullet tip of the internal flexible core of the vein and tubing passer preparatory to removing the rigid metal passer.
Figure 13B:
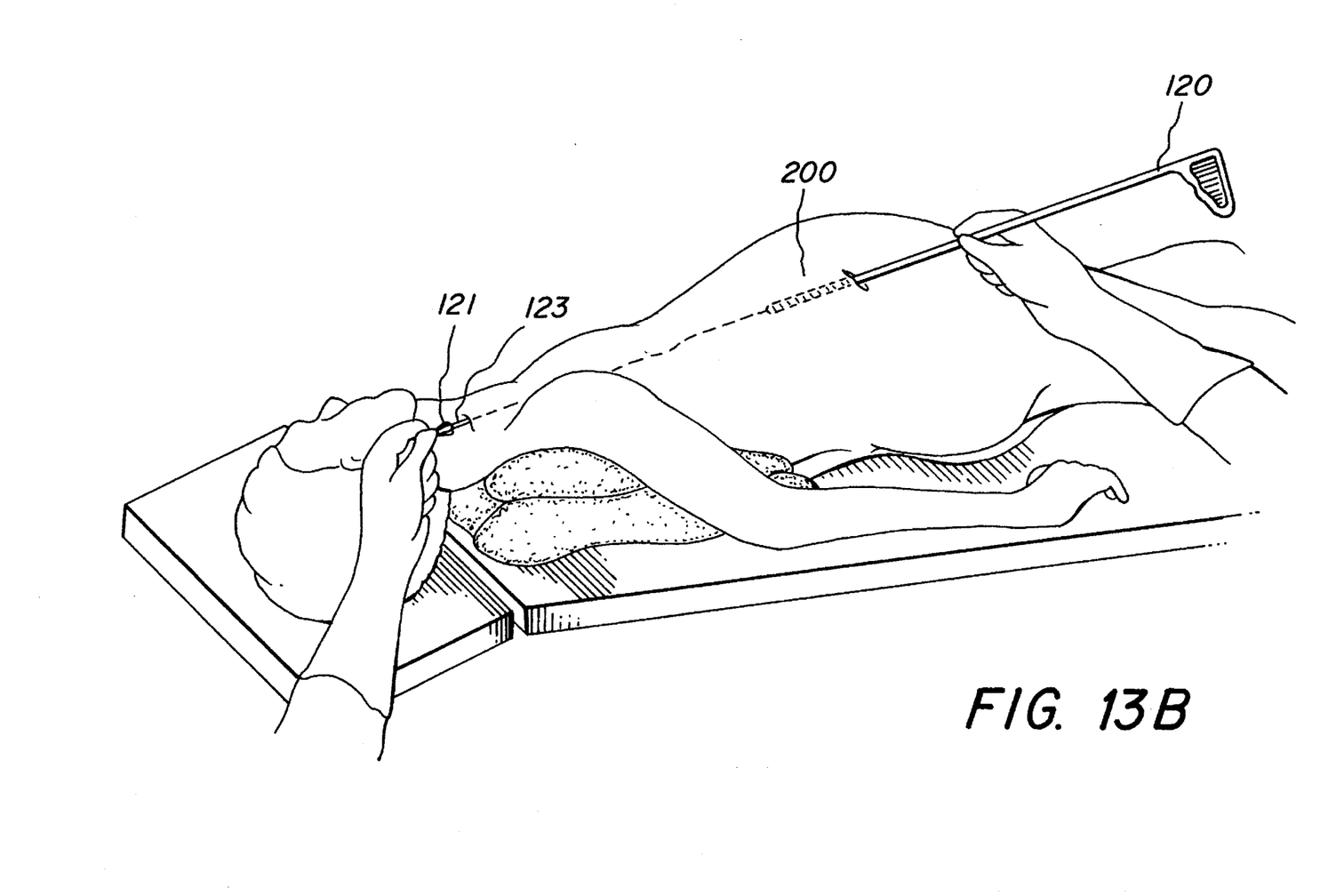
FIG. 13B shows the schematic representation of a sequential step required to bring the venous tubing from an abdominal incision into a neck incision using the vein and tubing passer of U.S. Pat. No. 4,418,693, in which the rigid metal tube is withdrawn leaving the flexible inner core in the subcutaneous tunnel, the venous tubing being affixed to a nipple attached on the end of the flexible core.
Figure 13C:
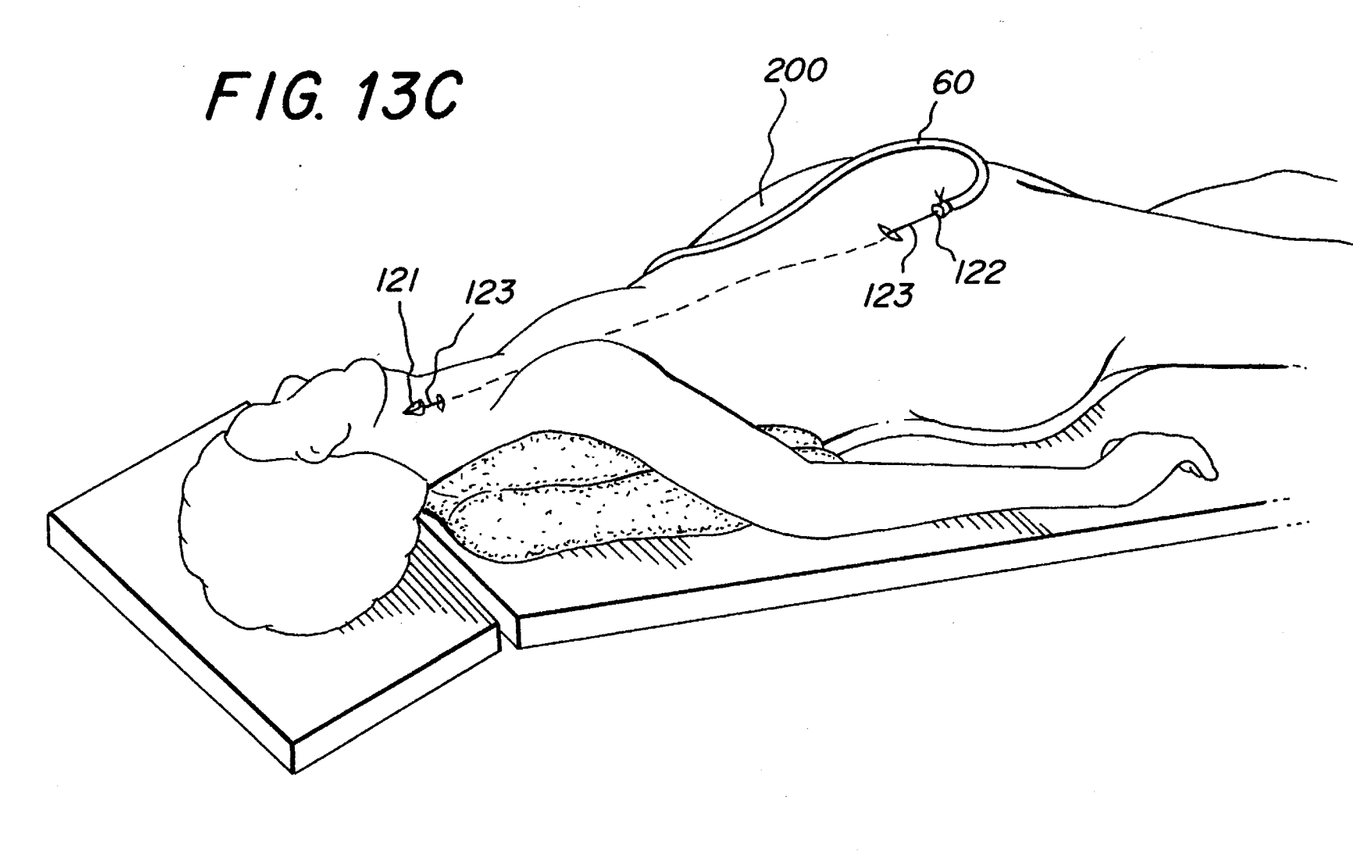
FIG. 13C shows the schematic representation of a sequential step required to bring the venous tubing from an abdominal incision into a neck incision using the vein and tubing passer of U.S. Pat. No. 4,418,693, with traction on the bullet tip in the neck wound pulling the venous tubing from the abdominal wound to the neck wound.
Figure 13D:
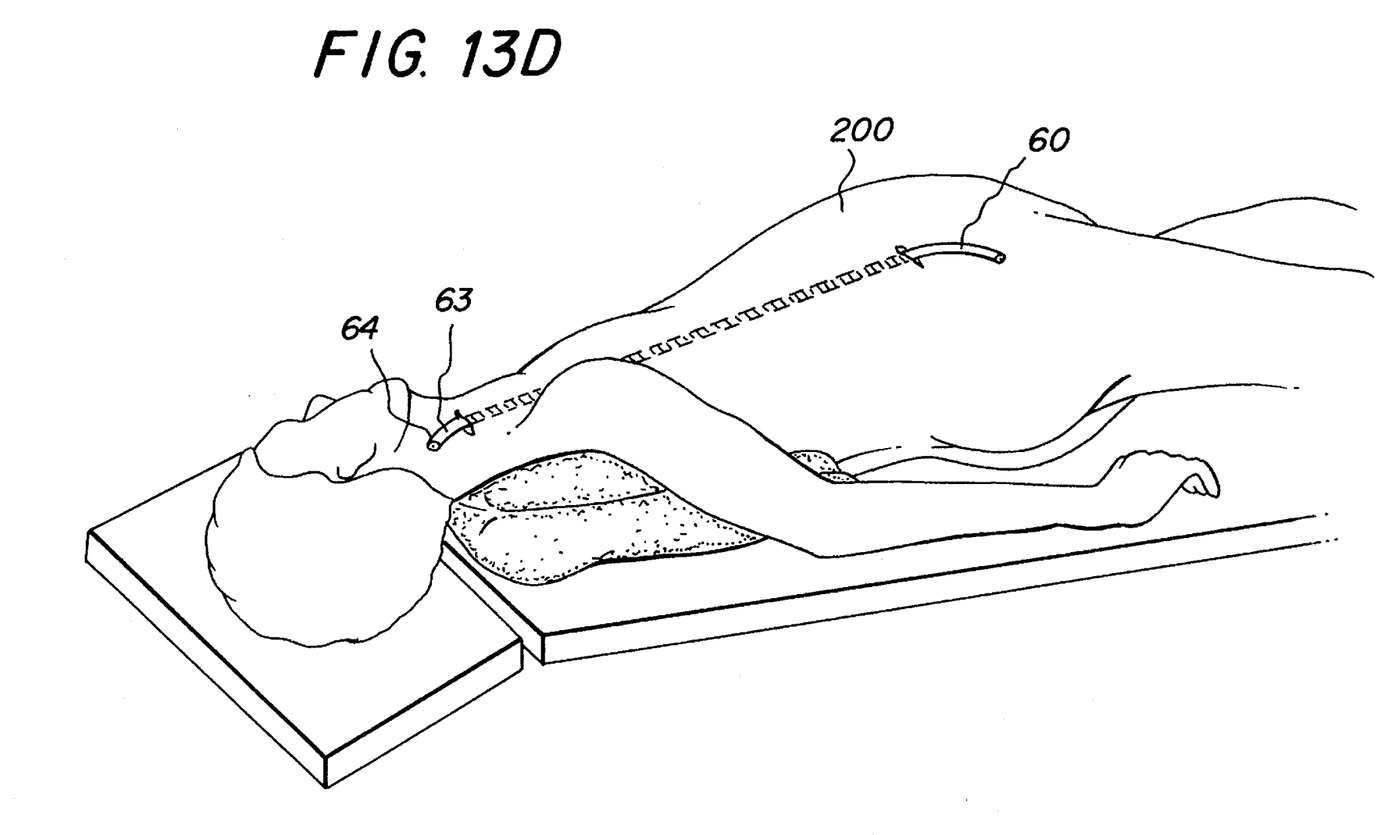
FIG. 13D shows the schematic representation of a sequential step required to bring the venous tubing from an abdominal incision into a neck incision using the vein and tubing passer of U.S. Pat. No. 4,418,693, in which the venous tube in the subcutaneous tunnel is disconnected from the flexible inner core of the vein and tubing passer.

In the next step, a tunnel is made with a vein and tubing passer designed for this purpose as is disclosed in U.S. Pat. No. 4,418,693 which is incorporated by reference into this application. FIGS. 13A–D show the schematic representation of the steps required to bring the venous tubing from an abdominal incision in to a neck incision using the vein and tubing passer of U.S. Pat. No. 4,418,693. in FIG. 13A, the rigid metal tube 120 is thrust through the subcutaneous tissue from an abdominal wound into a neck wound. The surgeon grasps the bullet tip 121 of the internal flexible core of the vein and tubing passer 123 preparatory to removing the rigid metal passer 120. In FIG. 13B, the rigid metal tube 120 is being withdrawn leaving the flexible inner core 123 in the subcutaneous tunnel. The venous tubing is affixed to a nipple 122 attached on the end of the flexible core 123. Traction on the bullet tip 121 in the neck wound pulls the venous tubing 60 from the abdominal wound to the neck wound. The tip of the venous tubing 63 is then inserted into the internal jugular vein (or subclavian vein if that route is chosen). FIG. 13D shows the venous tube 60 in the subcutaneous tunnel disconnected from the flexible inner core 123 of the vein and tubing passer. The venous tubing is inserted into the vein using the Seldinger technique.

Figures 14, 15:
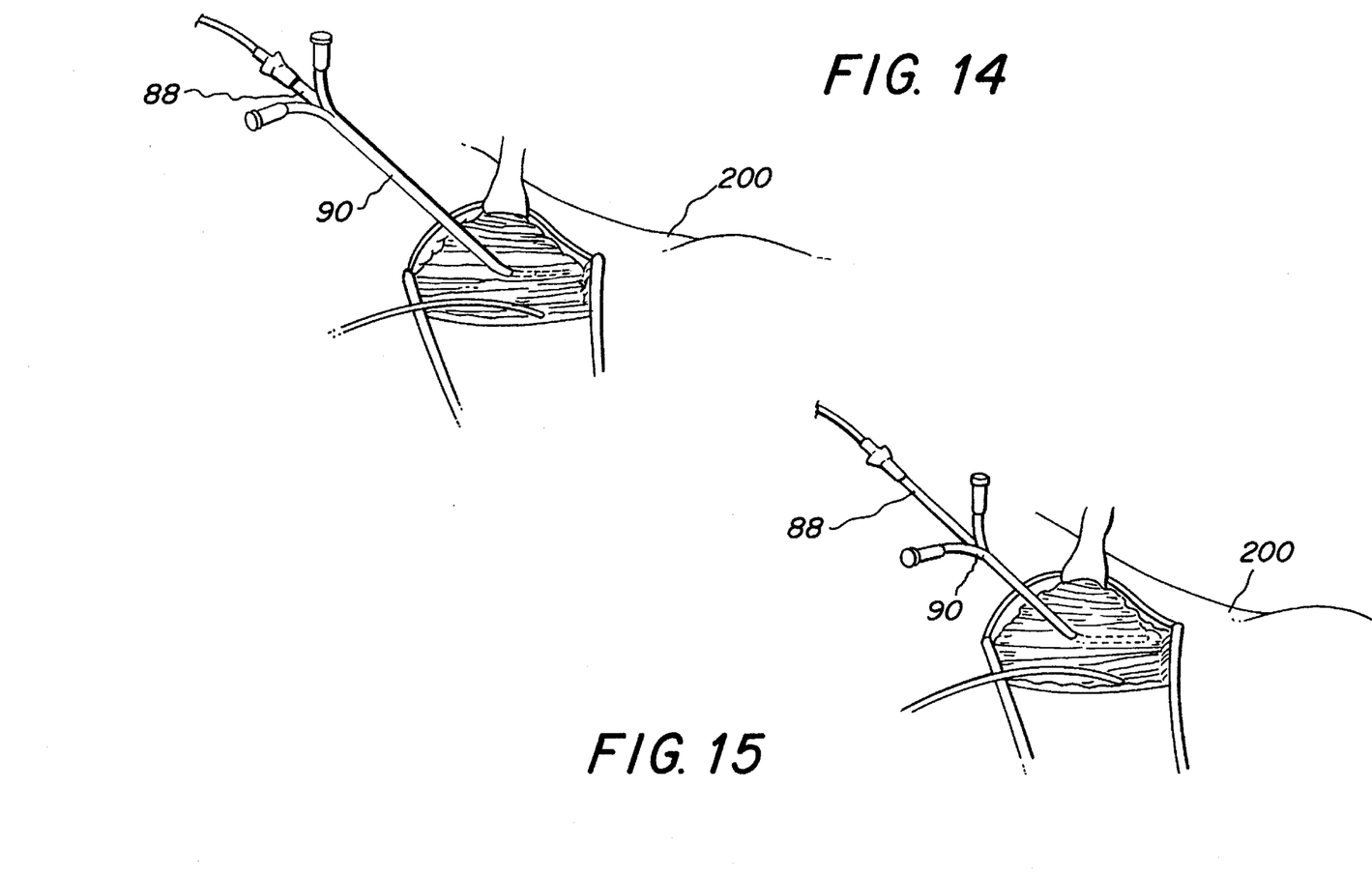
FIG. 14 shows schematic placement of the introducer, dilator and guide wire into the jugular vein.
FIG. 15 shows schematic sequential removal of the guide wire and dilator.

FIG. 14 shows the introducer 88 having been placed over the guide wire into the jugular vein and FIG. 15 shows the guide wire removed and dilator 90 being removed leaving the introducer.

Figures 16, 17:
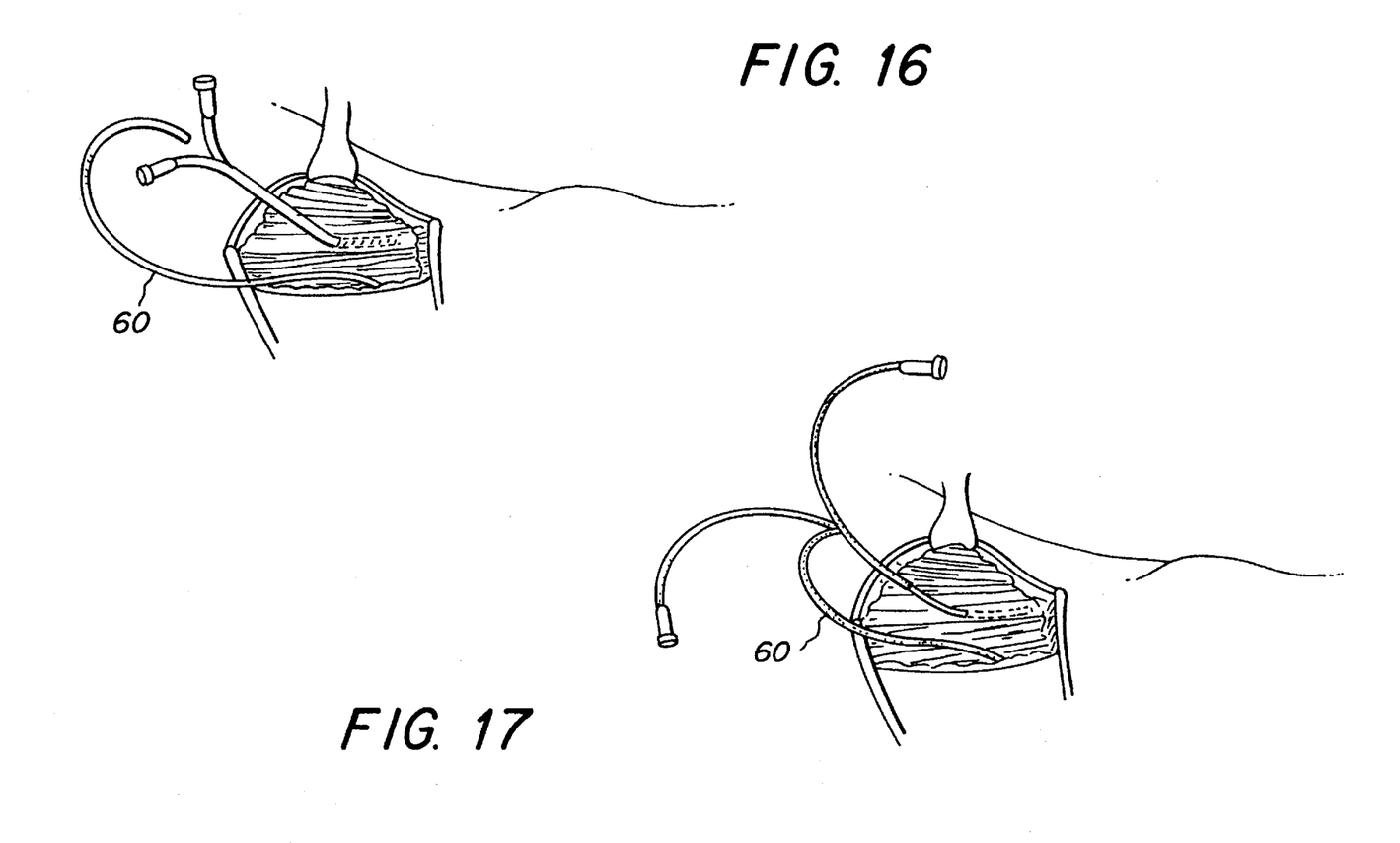
FIG. 16 shows schematic sequential insertion of the venous tubing through the introducer.
FIG. 17 shows schematic sequential peeling away of the introducer leaving the venous tubing in the jugular vein.

In FIG. 16 the venous tubing 60 is inserted through the introducer.

In FIG. 17 the introducer has been removed, leaving the venous tubing 60 in the jugular vein and the introducer is being peeled off the venous tubing. The venous tubing is not attached to the outlet port 61 of the valve 40 until the venous tube has been properly positioned in the thorax as subsequently described.

The inside and outside surfaces of the plastic venous tubing 60 are treated to prevent clot formation on the outside of the indwelling venous tubing. One method involves bonding of a hydrophilic colloid to the surface of the venous tubing. For instance, polyvinylpyrolidone can be chemically bonded to the surface of the venous tubing by radiation. An alternative is the sulphonation of the plastic surface. These treatments render the plastic surface water wettable and less likely to induce platelet activation and clotting. The presence of a hydrophillic colloid on the surface of the tubing renders it thrombus resistant. The surface treatment may also be by sulphonation which in addition to rendering the surface wettable with water possesses unique anticoagulant properties. These treatments have an added advantage in that they prevent air bubbles from adhering to the surface of the tubing. Small bubbles are often difficult to dislodge. The venous tubing 60 also has metered radiopaque markers located in the wall of the tubing allowing identification by radiography together with linear measurement which makes it possible to quantitate an exact length of tubing that must be inserted or withdrawn to position the tip of the venous tube at a selected target. The markers which are placed in the transverse direction will quantitatively detect the extent of malplacement of the tubing by radiography while the patient is on the operating table. This often spares the patient subsequent surgery to correct an inadvertent malplacement. The rigid transverse markers are placed at stated intervals of 2 to 3 mm. The transverse rigid bands 62 render the flexible venous tubing kinkproof as described in U.S. Pat. No. 4,662,404 which is incorporated herein by reference. In addition, the markers are spaced exactly to measure distance. The kink proof feature is important when the venous tubing must make an acute bend of 180° to enter the jugular vein. The kink proof feature allows the tubing to have a much thinner wall thickness. Thin tubing is much more susceptible to kinking and therefore flexible tubing must have an appreciable wall thickness to prevent this. With thin walled tubing, the internal lumen can be larger or the outside diameter reduced. As noted by U.S. Pat. No. 4,662,404, when the tubing is kink proof even thin walled tubing does not kink. This kink proof feature is especially important in children where the 180° bend must be quite acute. In addition to these safeguards, the tip 63 of the venous tubing 62 contains a small ring of ferrite 64 which is incorporated into the wall of the tubing. This enables the surgeon to detect the position of the venous tip on the operating table either with or without the use of X-rays. Without X-rays, the surgeon can detect the presence of the ferrite tip 63 of the tubing 60 with a modified Gauss meter, a so called dip meter. The knowledge that the tip of the tubing is in an area of rapid blood flow, such as the atrio-caval junction, is of extreme importance to the surgeon. When it has been ascertained that the tip of the venous tubing is in the proper location, the excess tubing is cut off and the venous tubing is connected to the outlet port 61 of the valve 40.

Figure 18:
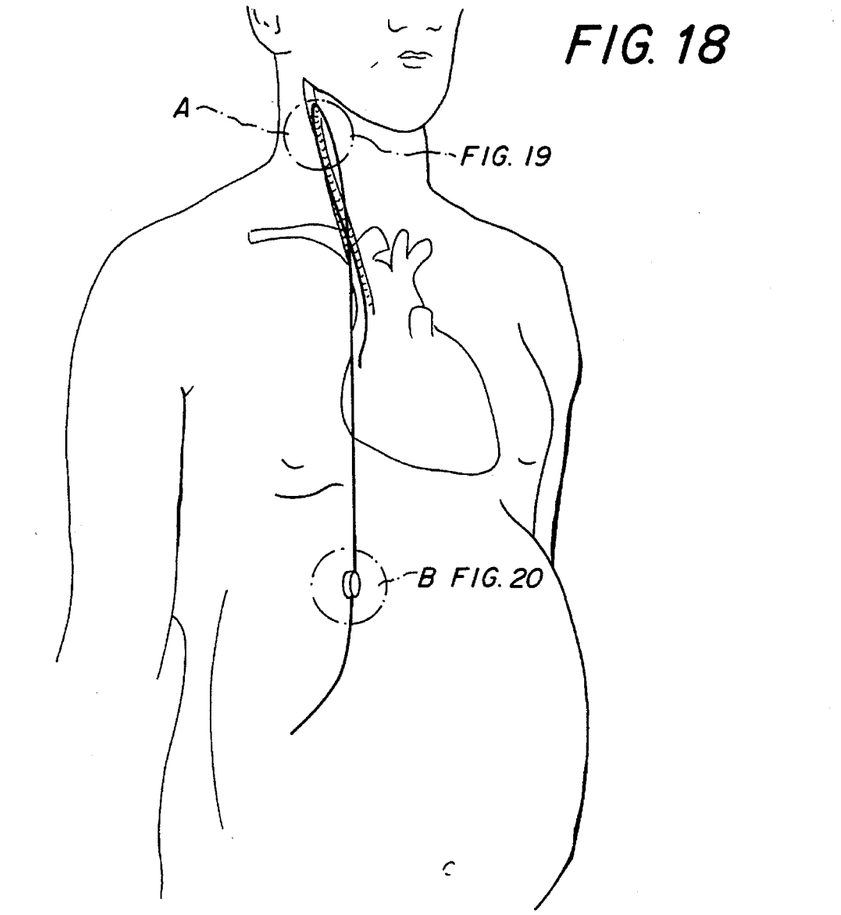
FIG. 18 is a schematic view of a patient after insertion of the inventive shunt assembly.
Figure 19:
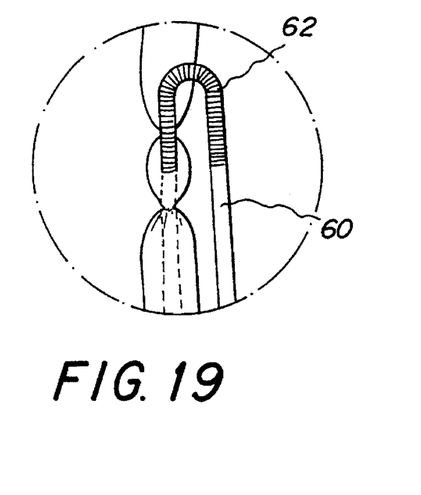
FIG. 19 is an exploded enlarged portion taken from circled area A in FIG. 18.
Figure 20:
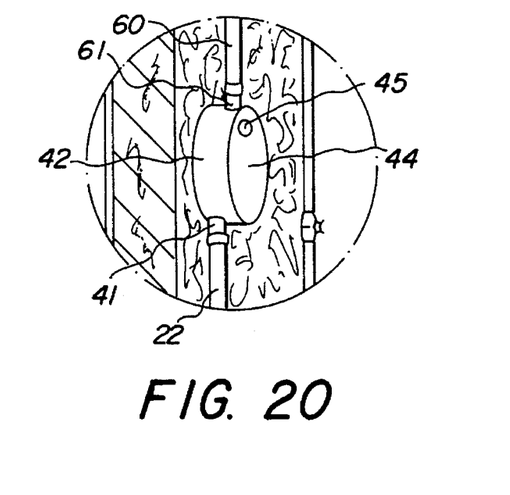
FIG. 20 is an exploded enlarged portion taken from circled area B in FIG. 18.

The completed operation is illustrated in FIG. 18 with enlargements of various aspects shown in FIGS. 19 and 20. Formerly, a great deal of time was required to insert a peritoneovenous shunt. Ascitic patients are weakened and tolerate prolonged surgery poorly. Therefore, the design of the shunt including the valve, the venous and peritoneal collecting tubes and the apparatus supplied for its insertion all must be designed for a rapid insertion. The present shunt allows for percutaneous insertion of the tubes. The shunt and all of the tools required for rapid insertion are supplied to the surgeon as an integral unit in kit form.

FIG. 18 is a schematic view of a patient after insertion of the ascites valve. The venous tube extends from the atriocaval junction down to the valve which is implanted subcutaneously parallel with the largest plane of the valve imbedded in the subcutaneous tissue parallel to the skin and muscle layers. The peritoneal tube extends from the lower end of the valve into the peritoneal cavity. The skin and subcutaneous tissue cover the valve without causing a protusion.

In the foregoing description, the invention has been described with reference to a particular preferred embodiment, although it is to be understood that specific details shown are merely illustrative, and the invention may be carried out in other ways without departing from the true spirit and scope of the following claims.

What we claim is:

1. A device for the transfer of body fluids which accumulate in the peritoneum cavity into the vascular system comprising a peritoneal tube connected to an inlet located on the side of a hollow plastic flat surfaced implantable valve means, pressure differentials in fluids from the peritoneum cavity causing said valve means to open and pass the fluid under pressure therethrough into a venous tubing connected to an outlet located on the side of the flat surfaced valve means and through said venous tubing, said venous tubing being provided with a rigid radiopaque marker means and a ferrite means located near the distal end of the venous tubing, the tip of which is positioned in a major intrathoracic vein through an accessible vein outside the thorax of a patient, said valve means comprising a plastic housing with inlet means and outlet means and a valve seat means, said peritoneal tube mounted to said inlet means and a venous tube mounted to said outlet means, said valve means including a valve member having a valve stem and a flexible diaphragm section on one end of said valve stem and a strut assembly on its other end, said flexible diaphragm section resting against said valve seat means in a normally closed position, said flexible diaphragm section moving away from said valve seat means in response to pressure exerted thereon to permit flow of the body fluid from the peritoneum through the valve housing and into the venous tube which empties into an intrathoracic vein.

2. A device for the transfer of body fluids which accumulate in the peritoneum cavity into the vascular system comprising a peritoneal tube connected to an inlet of a thin disc shaped plastic implantable valve means, said valve means comprising a plastic cylindrical housing defining a chamber with inlet means and a second chamber with outlet means, a valve seat means mounted on an intermediate support member secured in said housing, a moveable valve member seated on said valve seat in a normally closed position and cover members mounted on each end of said cylindrical housing, one of said cover members holding a silicon injection plug, pressure differentials in fluids from the peritoneum cavity causing said valve member to open and pass the fluid into and through a venous tubing which is connected through the access vein of a patient so that the tip lies in a major thoracic vein, said peritoneal tube mounted to said inlet means and a venous tube mounted to said outlet means, said valve member including a flexible diaphragm section which rests against said valve seat means in a normally closed position and which diaphragm section moves away from said valve seat means in response to pressure exerted thereon to permit flow of the body fluid from the peritoneum through the valve housing and into the venous tube which empties into an intrathoracic vein.

3. An implantable valve for the treatment of ascites comprising a thin disc shaped housing with integral valve seat means defining reservoir chambers with respective inlet port means and exit port means, top and bottom covers secured to said housing, said top cover defining an aperture holding a soft silicon injection plug bonded thereto, said plug being self-sealing after needle puncture, a moveable valve seated in said housing seated on said valve seat means and held on said valve seat means in a normally closed condition, said moveable valve comprises a valve stem, a plurality of elastomeric struts extending outwardly from said valve stem, a rim member secured to said elastomeric struts, the thickness of said rim member together with the initial stress on the elastomeric struts setting the opening pressure, sensitivity and resistance to flow of the moveable valve and a diaphragm means mounted to one end of said valve stem, said moveable valve being adapted to move in response to differential pressure of 1–4 cm of water allowing fluid to flow from said inlet port means into said housing chamber and out said outlet port means.

4. A valve according to claim 3 wherein said inlet port and exit port means are hollow nipple members which extend outward from said housing.

5. A valve according to claim 3 wherein said diaphragm means is a conical shaped or curvilinar dome member adapted to seat on a conforming valve seat means.

6. A valve according to claim 3 wherein said housing is made of transparent biocompatible plastic.

7. A valve according to claim 6 wherein said transparent biocompatible plastic is polysulphone.

8. A valve for patient inplantation suitable for the treatment of ascites and hydrocephalus comprising a thin housing with an integrally molded conical valve seat and a cylindrical valve retaining wall encircling said conical valve seat, said housing defining separated chambers, one of which is provided with inlet port means and another being provided with exit port means, top and bottom covers secured to said housing, at least one of said covers being provided with an aperture containing an injection plug, a moveable diaphragm valve seated in said housing and held in place by projection means extending from one of said covers, said moveable diaphragm valve being normally seated on a valve seat conforming to the shape of the diaphragm and held on said conforming valve seat in a normally closed condition, said valve being adapted to move away from said valve seat in response to a preset differential fluid pressure which can vary from 1 to 20 cm of water allowing fluid to flow from said inlet port means into said housing and out said outlet port means.

9. A shunt assembly for draining body fluids which accumulate in the peritoneum cavity of a patient into the venous system using the differential pressure between major intrathoracic veins and the atmospheric pressure shared by other fluids in the body comprising a peritoneal tube connected to the inlet chamber of a plastic valve means with one end being positioned in the peritoneum, so that pressurized fluid transported from the peritoneum cavity will cause the valve means to open and pass the fluid under pressure into an outlet valve chamber and through a venous tubing which is connected thereto and into an access vein in the thorax of the patient, said valve means comprising a rigid plastic thin disc shaped housing defining two separated chambers, one with inlet port means and the other with exit port means, top and bottom planar lids secured to said housing, said top lid defining an aperture holding a soft self sealing elastomeric plug, a moveable elastomeric valve member seated in said housing adapted to move allowing fluid to flow from said inlet port housing chamber and into said outlet port housing chamber, said elastomeric valve member moveably seated in said housing, said valve means also including a stem with a flexible diaphragm means secured to one end which rests against a valve seat formed in said housing and which flexible diaphragm means moves away from said valve seat in response to a differential pressure exerted on it thereby permitting flow of the body fluid from the peritoneum through the valve housing and outlet ports through the venous tube into an intrathoracic vein.

10. A shunt assembly for draining body fluids which accumulate in the peritoneum cavity of a patient into the venous system using the differential pressure between major intrathoracic veins and the atmospheric pressure shared by other fluids in the body comprising a peritoneal tube connected to the inlet chamber of a plastic valve means with one end being positioned in the peritoneum, so that pressurized fluid transported from the peritoneum cavity will cause the valve means to open and pass the fluid under pressure into an outlet valve chamber and through a venous tubing which is connected thereto and into an access vein in the thorax of the patient, said venous tubing including a soft self-sealing silicon bubble positioned near said valve plastic housing outlet means, said valve means comprising a rigid plastic thin disc shaped housing defining two separated chambers, one with inlet port means and the other with exit port means, top and bottom planar lids secured to said housing, a moveable elastomeric valve member seated in said housing adapted to move allowing fluid to flow from said inlet port housing chamber and into said outlet port housing chamber, said elastomeric valve member moveably seated in said housing, said valve means also including a stem with a flexible diaphragm means secured to one end which rests against a valve seat formed in said housing and which flexible diaphragm means moves away from said valve seat in response to a differential pressure exerted on it thereby permitting flow of the body fluid from the peritoneum through the valve housing and outlet ports through the venous tube into an intrathoracic vein.

* * * * *